United States Patent [19]

McAleer et al.

[11] Patent Number: 5,264,106
[45] Date of Patent: Nov. 23, 1993

[54] ENHANCED AMPEROMETRIC SENSOR

[75] Inventors: Jerome F. McAleer, Wantage; John T. Law; Richard A. Morris, both of Abingdon; Lesley Scott, Witney; John M. Mellor, Southampton; Manus Dennison, Abingdon, all of Great Britain

[73] Assignee: Medisense, Inc., Waltham, Mass.

[21] Appl. No.: 33,422

[22] Filed: Mar. 18, 1993

Related U.S. Application Data

[63] Continuation of Ser. No. 886,306, May 21, 1992, which is a continuation of Ser. No. 768,358, Sep. 30, 1991, abandoned, which is a continuation of Ser. No. 417,262, Oct. 5, 1989.

[30] Foreign Application Priority Data

Oct. 7, 1988 [GB] United Kingdom ............... 8823569
May 31, 1989 [GB] United Kingdom ............... 8912463

[51] Int. Cl.$^5$ ............................................. G01N 27/26
[52] U.S. Cl. ................................ 204/403; 204/153.12; 435/288; 435/291; 435/817
[58] Field of Search ................ 435/817, 288, 29; 204/153.12, 403

[56] References Cited

U.S. PATENT DOCUMENTS

| | | | |
|---|---|---|---|
| Re. 30,267 | 5/1980 | Bruschi | 436/170 |
| 4,476,005 | 10/1984 | Tokimaga et al. | 204/403 |
| 4,704,193 | 11/1987 | Bowers et al. | 204/153.12 |
| 4,758,323 | 7/1988 | Davis et al. | 204/403 |
| 4,795,707 | 1/1989 | Niiyama et al. | 435/288 |
| 4,830,959 | 5/1989 | McNeil et al. | 435/7 |
| 4,857,152 | 8/1989 | Armstrong et al. | 204/153.12 |
| 4,882,013 | 11/1989 | Turner et al. | 204/153.12 |
| 4,886,740 | 12/1989 | Vadgama | 435/4 |
| 4,890,620 | 1/1990 | Gough | 128/635 |
| 4,897,173 | 1/1990 | Nankai et al. | 204/403 |
| 4,919,767 | 4/1990 | Vadgama et al. | 204/153.12 |

FOREIGN PATENT DOCUMENTS 3347104 12/1983 Fed. Rep. of Germany.
1507810 4/1978 United Kingdom.

OTHER PUBLICATIONS

G. G. Guilbault et al., Anal. Chem., vol. 42, No. 14, pp. 1779-1783, Dec. 1970.
Partial Translation of German Patent 3347104.

*Primary Examiner*—John Niebling
*Assistant Examiner*—Bruce F. Bell
*Attorney, Agent, or Firm*—Fish & Richardson

[57] ABSTRACT

An amperometric sensor comprises a working electrode, a reference electrode, an enzyme whose catalytic activity on a substrate results in electroactivity, and an enhancer compound which enhances the detected electroactivity.

10 Claims, 1 Drawing Sheet

ENHANCED AMPEROMETRIC SENSOR

This is a file wrapper continuation of application Ser. No. 07/886,306 filed on May 21, 1992, for ENHANCED AMPEROMETRIC SENSOR, which is a continuation of Ser. No. 07/768,358 filed Sep. 30, 1991 (now abandoned), which is a continuation of Ser. No. 07/417,262 filed Oct. 5, 1989.

BACKGROUND OF THE INVENTION

The present invention relates to sensors, and more particularly to sensors with enhanced response.

Electrochemical sensors, and especially amperometric sensors are described, for example, in published European Patent Specifications 78636, 125137, and 184895, among others. Such sensors are based on enzyme systems, optionally with electron transfer agents to assist charge transfer, and can be used to detect, for example, naturally occurring metabolites such as glucose or cholesterol, or substances introduced to the body such as alcohol or a drug. In a typical mode of use, the system is set up so that there is a response at the amperometric electrochemical sensor which is dependent on the concentration of analyte.

The amperometric sensor can be constructed as a strip sensor, as described for instance in EP 127958. For preference, the strip element is a dry strip disposable test element, for use in conjunction with a read-out device to which the test element can be connected to give a reading of the analyte level after application of a sample to a target area of the test element. For example, the read-out device can be a hand-held or desk-top instrument.

After a predetermined incubation period to allow for reaction, a reading can be taken by poising the working electrode at a suitable voltage, and monitoring the resultant current for a set time. By reference to currents generated under standardised conditions with known concentrations of analyte, the current can be used to give a quantitative value of the analyte level.

Such amperometric strip sensors can be used to give a disposable strip sensor for glucose, as illustrated by the "ExacTech" (Trade Mark) sensor which is commercially available.

A mediator is not always necessary for an amperometric strip sensor. For example, EP 184895 describes a system for monitoring paracetamol. An electrode poised at a suitable potential is contacted with a sample suspected of containing an N-acylated primary aromatic amine, typically paracetamol, and with an enzyme capable of catalysing the hydrolysis of the N-acylated primary aromatic amine. The current flowing in the electrode is a measure of the quantity of hydrolysis products formed and thereby of the concentration of N-acylated primary aromatic amine in the sample.

In practice with the sensors of EP 184895, it is sometimes difficult to achieve reliable results when using blood samples from patients receiving medication for paracetamol overdose. This difficulty particularly arises, for instance, with patients receiving antidote treatment. The presence of the antidote interferes with the assay reaction.

More generally, with some enzyme systems which might be used in such an amperometric sensor, there is a problem that the product derived from the substrate by enzyme activity is an inhibitor of the enzyme. When the product inhibits the enzyme, there is reduced enzyme activity, leading to a reduction in the charge transfer which might otherwise be obtained.

OBJECTS OF THE INVENTION

It is an object of this invention to provide a new electrochemical sensor with an enhanced response for detection of a substrate. A further object is the provision of a strip sensor system with an overlay incorporating an enhancer compound. A related object is a sensor with an enhancer compound that can react with a product formed in an enzyme reaction and give extra electroactive compound itself detectable by the sensor. An alternate related object is a sensor with an enhancer compound which removes inhibitor produced by enzymatic modification of the substrate, and can lead to an increased signal in the analytical system.

SUMMARY OF THE INVENTION

In accordance with the present invention, an enhancer compound is incorporated in the sensor in order to lead to an increased signal in the analytical system.

To this end, the present invention provides an amperometric sensor comprising a working electrode, a reference electrode, an enzyme whose catalytic activity results in electroactivity, and an enhancer compound which enhances the detected electroactivity.

PREFERRED EMBODIMENTS OF THE INVENTION

Figure 1:
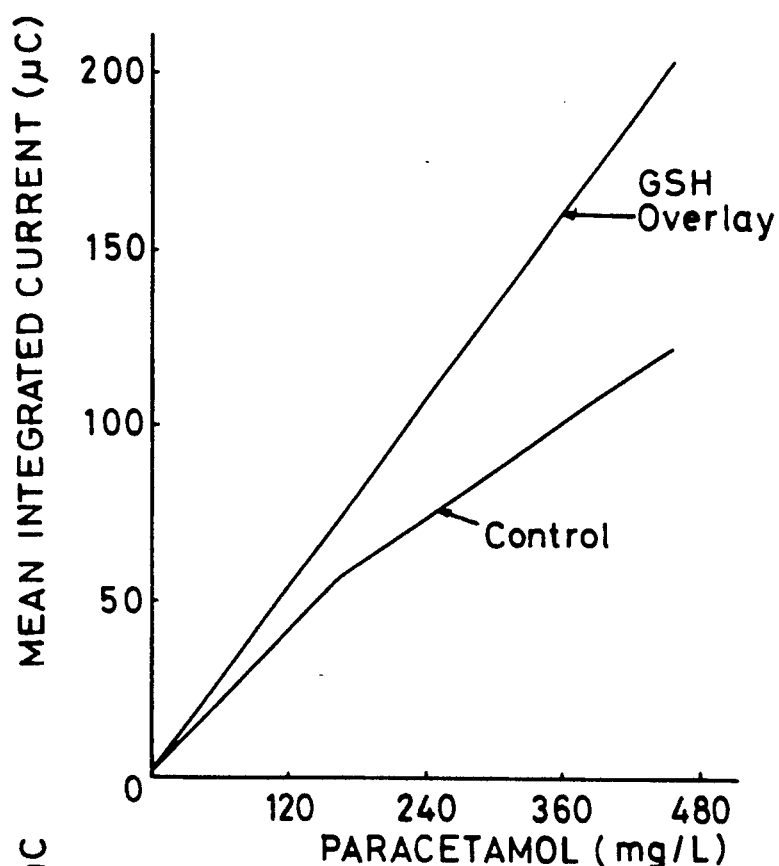
FIG. 1 is a graph of current versus concentration of paracetamol resulting from the experiment of Example 1, below.

In a preferred aspect, the amperometric assay system involves enzyme action on a substrate, and the enhancer compound reacts with the product to increase the current.

For example, the enhancer compound can serve to react with inhibiting or interfering compounds present in the system, including inhibiting compounds produced by enzyme action on the substrate. In this latter respect, the present invention is particularly appropriate for use with enzyme/substrate combinations where the enzyme is being employed to drive an equilibrium reaction in an unfavourable direction. In the invention, the removal of the product by further reaction with the enhancer compound has the effect of pulling the equilibrium in the desired direction.

In another example, the enhancer compound can serve to react with an electroinactive compound present in the system, in order to convert it to an electroactive compound. In this respect, the present invention is particularly appropriate for use with enzyme/substrate combinations where the enzyme acts on a substrate to give an electroactive compound. As part of the amperometric detection, such a compound is converted to an electroinactive compound. The enhancer compound can regenerate an electroactive compound, leading to increased current.

In many situations, when testing for suitable enhancer compounds, we have found that it is readily possible to obtain a false negative result. Specifically, we have found that there is the possibility that the enhancer compound might react not only with the intended component, but also with the enzyme itself. With such an enhancer compound, the possible enhancement of current is frustrated by accompanying reaction of the enhancer compound with the enzyme. Overall, the effect is to negate the current increase which might otherwise be achieved with the adoption of the enhancer compound.

The present invention seeks to avoid this problem, by presenting the enhancer compound in such a manner that it can react with the intended component but effectively not with the enzyme. This end can be achieved by separating the enhancer compound from the enzyme.

To this end, the enhancer compound can be contained, for example, in one or more extra, porous layers, such as an overlay, of the strip. The one or more extra layers can be made, for example, of cellulose, nylon, polyester or other man-made fibres. The porosity can be selected as desired, for example in order to let through whole blood or to let through plasma or serum. The enhancer layer is preferably coated with surfactant, such as a non-ionic surfactant, and effectively serves to pull the plasma or serum through to the electrodes.

For preference, the layer containing the enhancer compound is of cellulosic paper. The nature of the paper is not critical, but typically it is a cellulose paper such as those available for the manufacture of tea-bags or for the manufacture of indicator papers. The selected material can be impregnated or otherwise coated with a solution of the enhancer compound.

The paper or other overlay with the enhancer compound can be used in conjunction with other overlying layers. For instance, a protective mesh can be employed on the outer face of the sensor. The mesh is preferable coated with surfactant in to wet the sample over the face of the target area sensor, while acting as a preliminary filter and protecting the underlying layers. The mesh can be of polymer, for example nylon or polyester, and the surfactant is typically a non-ionic surfactant, more especially a polyoxyethylene derivative.

In fabricating a sensor of the present invention, the existing knowledge can be taken into account concerning enzymes, enzyme substrates, etc. In this respect, reference is made, for example, to the published European patent Specifications in the name of MediSense, Inc (formerly Genetics International Inc), and related literature, such as the book Biosensors Fundamentals and Applications, eds Turner, Karube and Wilson, OUP 1987.

The electrochemical sensor is preferably one which involves amperometric detection, and preferably utilizes a strip element, especially a throw-away dry strip. Accordingly the sensor electrodes preferably comprise electrode areas formed for instance by screen printing, spraying, or other suitable deposition technique.

For preference, a disposable test element carries a working electrode incorporating the appropriate test reagents for generation of a current indicative of the level of analyte, and a reference electrode. Typically, in the test element, the test reagents are in one or more carbon-based layers. The respective carbon mixtures are applied on to a conductive track on a support, for example in close proximity to a reference electrode mixture connected to a second track. In this way, a sensor is produced which is capable of working with a small sample of blood or other liquid covering the effective electrode areas. The mixtures can be suitably applied by screen printing.

In a particularly preferred embodiment, the present invention provides a dry strip sensor which comprises an elongate, electrically-insulating substrate having a pair of longitudinal, substantially parallel, electrically-conducting tracks thereupon, each track being provided at the same end with means for electrical connection to a read-out means and provided with an electrode, one of the electrodes being the reference electrode and the other being the working electrode with test reagents.

More especially, such a sensor is suitably configured in the form of a supporting strip of electrically insulating material such as a synthetic polymer (for instance pvc) carrying at a location between its ends the two electrodes supported on electrically conductive printed tracks. For example, the electrodes can take the form of two rectangular areas side by side on the strip. Such areas can be configured as a target area to be covered by a single drop of sample, such as blood, for testing for an analyte. If desired, non-rectangular electrode areas, for instance diamond-shaped, semicircular, or triangular areas, can be employed to provide a target area for optimised contact by a liquid sample.

Furthermore, in a variation in accordance with this invention, there is a third electrode similar to the working electrode but lacking the or at least one enzyme of the working electrode. Such a third electrode can lead to more reliable results, in that if charge passed at the third electrode is subtracted from charge passed at the working electrode, then the resulting charge is solely due to the reaction of interest.

In a typical manufacturing procedure of a preferred sensor, an adhesive can be screen printed or otherwise applied around the sample target area of each strip sensor followed by placement and adhesion over this area of paper coated with the enhancer compound. A protective mesh can be positioned over the enhancer layer and held in place by an insulation print applied generally to the test element in order to leave uncoated both the sample target area and terminal ends to be inserted in to a read-out device.

The present invention is illustrated by the use of enhancer compounds which react with inhibiting products of enzymatic reaction. In particular, but without being restrictive, the present invention relates to an alcohol sensor, where typically an alcohol dehydrogenase functions in the detection of ethyl alcohol as a substrate, in contrast to the typical enzyme reaction of this enzyme where the alcohol is the product. In the sensor, the alcohol dehydrogenase converts alcohol (ethanol) to acetaldehyde. The enzymatic activity of the dehydrogenase is accompanied by reduction of the enzyme cofactor $NAD^+$ to $NADH$, which in turn can be detected by transfer of charge from an electrode with the use of an electron transfer compound, such as a quinone, phenazine, or other aromatic compound. In this respect, reference is made to J Am Chem Soc (1985) 107, 479; U.S. Pat. No. 4,271,265; Analytical Biochemistry (1979) 99, 112; and J. Electroanal. Chem. 234 pp 163-173 1987.

In practice, the acetaldehyde is an inhibitor of the dehydrogenase, and so a poor response is obtained with change in the concentration of alcohol. Lack of linearity makes difficult the adoption of this system as an analytical sensor for alcohol.

Removal of acetaldehyde by chemical means has been investigated with the aim of improving the linearity of the assay. Trials with Schiff's base-forming reagents and mono-amines yielded little improvement. Assays using buffers incorporating alcohol and simple aliphatic diamines gave elevated current responses. However, the benefit was lost completely when the diamine was incorporated in the working electrode mix. Spectrophotometric experiments demonstrated that the diamine was removing acetaldehyde by chemical reation, but the diamine was also inactivating the alcohol dehydrogenase.

With the present invention, a diamine compound is employed, for instance in a porous overlay of the sensor. The diamine reacts with the acetaldehyde being produced in order to prevent inhibition of the dehydrogenase.

Typically, for the alcohol sensor, the diamine compound is a diamine with two or three intervening atoms between the respective nitrogens of the diamine. It is proposed that the diamine be held in a porous overlayer above the working electrode. When a sample containing alcohol is applied to the electrode with diamine overlay, the diamine is released. It then reacts with acetaldehyde arising from the enzymatic oxidation of alcohol. For preference, the diamine is coated on the porous material together with a surfactant.

This invention is not limited to enhancer compounds which remove inhibiting products. Sequestering agents can be employed to remove or retard other components which interfere with the amperometric assay. Furthermore, the enhancer compound can serve to modify the product to increase its electrochemical activity.

In particular, but without being restrictive, the present invention relates to a paracetamol sensor. For the basic construction of such a sensor, the reader is referred, for example, to EP 184895.

Thus, in a specific aspect, this invention provides an electrochemical sensor for paracetamol which employs an enhancer compound to overcome interference by antidote treatment. A suitable enhancer compound for a paracetamol sensor is a thiol-containing compound. The nature of the thiol compound is not particularly critical. For example, the thiol compound can be glutathione, N-acetylcysteine, cysteine, dithiothreitol, mercaptoethanol, or other thiol compound generally conforming with the formula R-SH.

Without being bound by theory, it is hypothesised that the electrochemical detection of paracetamol ordinarily proceeds in accordance with the following reaction scheme, resulting in formation of electroactive p-aminophenol which is converted to electroinactive quinoneimine:

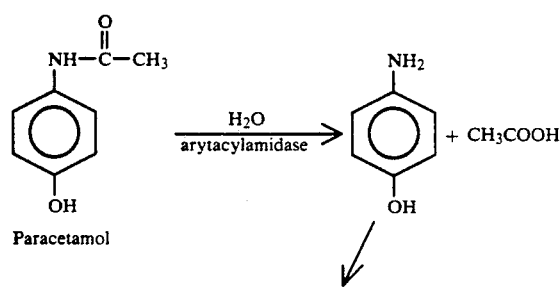
Paracetamol

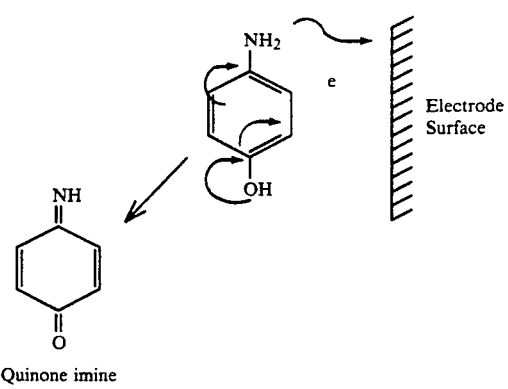
Quinone imine

It is then further hypothesised that in the presence of a thiol compound R-SH, the quinoneimine is converted to an electroactive p-aminophenol substituted with a thio group—SR, which in turn forms an electroinactive substituted quinoneimine, and so on as shown in the following reaction scheme:

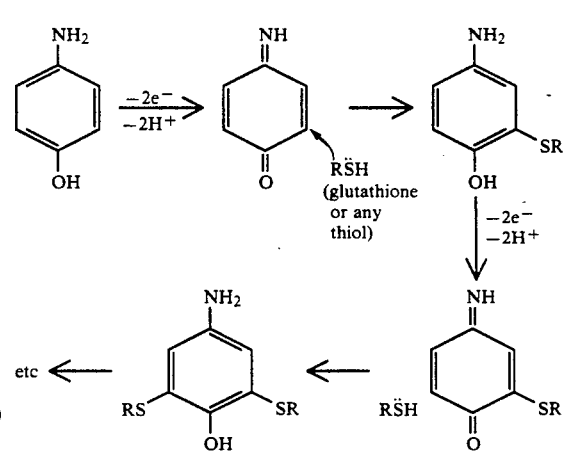

Regardless of hypothesis, it is observed that higher currents and more reliable results are achieved when the thiol compound R-SH is present in the assay system.

The present invention is thus particularly appropriate for use with enzyme/substrate combinations where the electroactive product of the enzyme reaction can be converted back to an electroactive compound by the enhancer after the redox reaction at the working electrode gives an electroinactive compound. In the invention, the generation of fresh electroactive compound gives the desired enhancement of response.

EXAMPLES OF THE INVENTION

The present invention is illustrated by the following Examples.

EXAMPLE 1

A disposable strip sensor for paracetamol was produced in accordance with EP184895. Multiple test elements were prepared by printing on to a sheet of pvc plastics material. For each test element, parallel electrically conducting tracks were laid down and then overprinted to form the working electrode and the reference electrode. The target area of each electrode was then defined with an insulation print.

Pieces of paper were dipped into a solution of 0.5-2.5% surfactant, 0.2M BES buffer (pH 7.45), and 10-100 mm glutathione. The paper was then allowed to dry. A glue was printed around the target area of each test element followed by placement and adhesion of the coated paper over this area. A nylon mesh impregnated with the same surfactant as the paper layer was then placed over the paper and held in place by two final insulation prints applied generally to the test element in order to leave uncoated the target area and the terminal ends to be inserted in to a read-out device.

Results obtained with the sensors of this invention in comparison with a control sensor lacking the overlay are shown in the accompanying FIG. 1. It will be seen that the response ("GSH overlay") of the sensor of this invention was more linear and gave a greater integrated current, in comparison with the response ("Control") of the control electrode.

EXAMPLE 2 (Comparative)

(a) Test Elements

Multiple test elements for alcohol were prepared by printing and then subdividing a sheet of pvc plastics material. For each test element, parallel electrically conducting tracks were laid down and then overprinted to form the working electrode and the reference electrode. For the working electrode, the following print mix was employed:

2.25 g carbon powder
1.5 g gelling agent
0.225 g surfactant
0.225 g electron transfer compound 3.7 g NAD+
200000-1000000 U alcohol dehydrogenase
7.2 g buffer The current was then measured with variation in alcohol level. A poor response was obtained, indicating unsuitability for analytical use.

(b) Test Elements with Diamine

Ethylene diamine dihydrochloride was added to the buffer of the working electrode formulation of Example 2 at concentrations of 20% and 30% (w/v). Electrode strips for detection of alcohol were produced as before. When tested, these electrodes gave no response.

Subsequent investigation demonstrated that ethylenediamine was a potent inhibitor of the alcohol dehydrogenase. Similar findings were obtained with many other amine compounds. These results clearly demonstrate that incorporation of the diamine directly into the working electrode does not produce a viable alcohol strip.

In a series of further experiments, the working electrode of the test element of the kind produced in (a) was overprinted with one or two further layers containing carbon powder and varying concentrations of ethylene diamine hydrochloride. The first overlayer contained 0%, 10% or 20% diamine, and the second overlayer contained 10% or 20% diamine.

In general, effective electrodes were not obtained.

EXAMPLE 3

An alternative approach involved dipping strips of filter paper into a 10% w/v solution of ethylenediamine in 0.2M BES buffer at pH 7.5 and then allowing them to dry. They were then placed over strips produced as described in Example 2(a), and alcohol solution applied to the test area. These showed enhanced currents and a more linear response, indicating that a layering approach may well be successful.

Initial optimization work involved finding a suitable and reproducible method for placing the coated layer over the alcohol strip. This work involved printing an aqueous-based glue around the target area of the strip followed by placement and adhesion of the coated layer over this area. A nylon mesh was then placed over the diamine layer and held in place by a final insulation print.

EXAMPLE 4

A range of diamines was obtained, as follows:
1. 2,5-diaminopyridine dihydrochloride
2. 1,2-diamino-2-methylpropane
3. 1,3-diaminopropane dihydrochloride
4. 3,5-diaminobenzoic acid dihydrochloride
5. 1,2-diaminopropane
6. m-xylylenediamine
7. ethylene diamine Initial studies involved preparing a range of concentrations of the compounds in buffers at pH 6.5 and 7.5 and adding various amounts of alcohol. These were tested on strips produced as described in Example 2(a), and were shown to produce enhanced currents (up to 80 mA).

Further studies were performed to evaluate the most effective of the diamine compounds for removing acetaldehyde from the reaction mixture solutions. These experiments were performed at both pH 6.5 and 7.5.

Of the compounds tested the following potencies were obtained:

compound (2) > compound (3) > compound (5) = compound (7)

Compound (2), 1,2-diamino-2-methylpropane, is therefore preferred.

The data, when considered in conjunction with the results obtained by adding alcohol/diamine solutions to strips produced as described in Example 2, showed a trend. There was a correlation between effectiveness of the compound and the ability to form 5- or 6-membered ring structures.

This might be attributable to the fact that the reaction between the diamine and acetaldehyde is a two step mechanism:

1) Initial attachment of the free amine on to the carbonyl carbon of acetaldehyde.
2) Ring closure to form a 5 or 6 membered ring system.

If step (1) is reversible, but step (2) is not reversible, then the effectiveness of the diamines can be rationalised. The potency of Compound (2) is then due to the steric orientation of the —NH$_2$ groups in juxtaposition which gave improved complexation ability.

EXAMPLE 5

A cellulosic tea-bag material (Schoeller and Hoesch 121) was dip coated in a 10% solution of 1,2-diamino-2-methylpropane buffered at pH 7.5, containing 1% (by vol) of a polyoxyethylene-alkyl ether surfactant. The material was air dried for 12 hours at room temperature before being placed over the working electrode. It was held in position by an adhesive which was screen-printed on the periphery of the working electrode of a test element prepared in accordance with Example 2(a).

Figure 2:
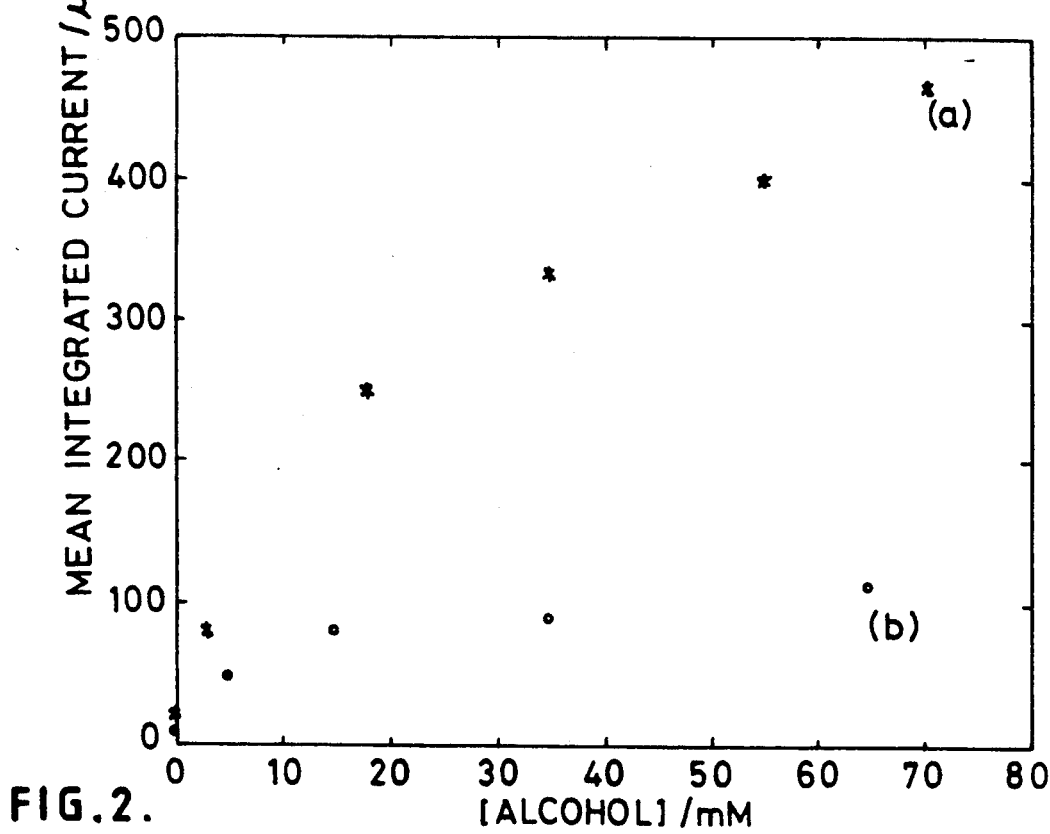
FIG. 2 is a graph of current versus concentration of alcohol resulting from the experiment of Example 5, below.

In FIG. 2, the results (a) with this electrode are compared with the results (b) for the electrode without overlay. The data demonstrate that the use of an overlay gives a more linear calibration.

We claim:

1. An amperometric sensor for ethyl alcohol comprising a working electrode, an alcohol dehydrogenase, a reference electrode, an electron transfer compound, and a diamine compound disposed such that it reacts with a product formed by the action of said alcohol dehydrogenase but is essentially unable to react with said alcohol dehydrogenase, said alcohol dehydrogenase acting to convert alcohol to acetaldehyde and said electron transfer compound transferring electrons produced in said conversion to said working electrode, said electrodes thus developing a current indicative of the level of alcohol in a sample.

2. The sensor of claim 1, wherein said diamine compound has 2 or 3 intervening carbon atoms between the nitrogens of said diamine.

3. The sensor of claim 1, wherein said diamine compound is contained in a porous layer overlaying a layer containing said alcohol dehydrogenase.

4. The sensor of claim 3, wherein said porous layer comprises said diamine compound and a surfactant.

5. The sensor of claim 3, wherein said porous layer comprises a cellulosic paper.

6. The sensor of claim 1, further comprising a protective mesh on the outer face of the sensor.

7. The sensor of claim 1, further comprising a throw-away dry strip element which comprises said electrodes and wherein said electrodes are deposited electrodes.

8. The sensor of claim 7, wherein said working electrode comprises said alcohol dehydrogenase and an electron transfer compound.

9. The sensor of claim 8, further comprising a third electrode.

10. A method of amperometrically assaying alcohol in a sample comprising supplying the sensor of claim 1, contacting a sample with said sensor, and sending the current flow from said sensor.

* * * * *